United States Patent
Sequeira et al.

[11] Patent Number: 5,879,711
[45] Date of Patent: Mar. 9, 1999

[54] STABLE ANTIANDROGENIC GEL COMPOSITION

[76] Inventors: Joel A. Sequeira, 6 Mary Ellen Dr., Edison, N.J. 08820; Fernand Labrie, 2989 De la Promenade, Ste-Foy (Québec), Canada, G1W 2J5; Shanshank Mahashabde, 49 nottingham Way, Somerset, N.J. 08873; Nicholas DeAngelis, 4099 Pierce La., Doylestown, Pa. 18901; Yves Merand, 3103 de Montreux, Ste-Foy, (Québec), Canada, G1W 3A1; Marc Fournier, 105, des Olivers, Lèvis (Québec), Canada, G6V 8W8

[21] Appl. No.: 966,263

[22] Filed: Nov. 7, 1997

[51] Int. Cl.⁶ .................. A61K 9/06; A61K 31/565; A61K 31/57; A61K 47/38
[52] U.S. Cl. .................. 424/488; 514/172; 514/177; 514/178; 514/859; 514/861; 514/876; 514/863; 514/864; 514/944
[58] Field of Search .................... 514/164–182, 514/859, 946

[56] References Cited

U.S. PATENT DOCUMENTS

| | | | |
|---|---|---|---|
| 3,290,293 | 12/1966 | Hirschmann . | |
| 3,332,967 | 7/1967 | Oliveto et al. . | |
| 3,341,527 | 9/1967 | Cross . | |
| 3,498,275 | 3/1970 | Oberster et al. . | |
| 4,220,775 | 9/1980 | Rasmusson et al. | 514/859 |
| 4,380,549 | 4/1983 | van Scott et al. | 514/23 |
| 4,775,529 | 10/1988 | Sequeira et al. | 514/179 |
| 5,116,615 | 5/1992 | Gokcen et al. | 424/94.2 |
| 5,525,594 | 6/1996 | Gourvest et al. | 514/25 |
| 5,536,714 | 6/1996 | Kojima et al. | 514/169 |
| 5,605,929 | 2/1997 | Liao et al. | 514/456 |
| 5,760,025 | 6/1998 | Kojima et al. | 514/169 |
| 5,770,223 | 6/1998 | Bonte et al. | 514/23 |

FOREIGN PATENT DOCUMENTS

| | | |
|---|---|---|
| 2001262 | 7/1970 | Germany . |
| 34 34 448A1 | 3/1986 | Germany . |
| 40 21433A1 | 11/1992 | Germany . |
| WO90/10462A1 | 9/1990 | WIPO . |
| WO91/00732A1 | 11/1991 | WIPO . |
| WO93/23053A1 | 11/1993 | WIPO . |
| WO94/26767A1 | 11/1994 | WIPO . |

*Primary Examiner*—Shep K. Rose
*Attorney, Agent, or Firm*—Thomas D. Hoffman

[57] ABSTRACT

Pharmaceutical compositions for the topical treatment of androgen-related conditions, e.g., acne in humans containing an amount of the compound represented by formula II effective for the topical treatment of the androgen-related conditions, e.g., acne

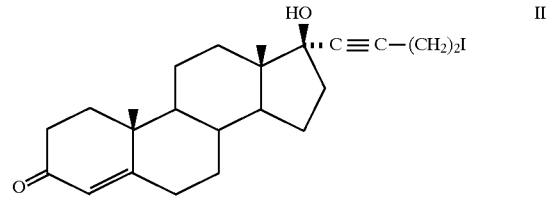

dissolved in an alcohol-water solvent system, such as ethanol-water [97.6:2.4(w/w)] and having an apparent pH in the range of about 3.5 to 4.5, and containing a gelling agent are disclosed.

20 Claims, No Drawings

STABLE ANTIANDROGENIC GEL COMPOSITION

BACKGROUND

This invention relates to stable pharmaceutical compositions in the form of a gel which are suitable for treating acne and other androgen-related conditions, including seborrhea, hirsutism, and androgenic alopecia, in humans and which contain an antiandrogen compound dissolved or suspended in an alcohol-water solvent system and having an apparent pH value of no more than about 5 and a gelling agent International Publication No. WO 94126767, published Nov. 24, 1994 discloses antiandrogens represented by the formula I

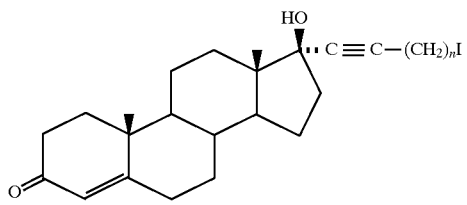

wherein n is an integer of 2 to 3, pharmaceutical compositions containing such antiandrogens and methods of using such antiandrogens to treat androgen-dependent diseases including acne.

In the course of development of a pharmaceutical composition containing one of the antiandrogenic compounds of formula I, it was discovered that this compound is unstable and decomposes over time even at 25° C.

Thus, there is a need for a stable pharmaceutical composition containing an antiandrogen useful for topical treatment of androgen-dependent diseases including acne and having an extended shelf life suitable for commercial use.

SUMMARY OF THE INVENTION

We have discovered that the compounds of formula I are more stable to decomposition in an alcohol-water solvent system containing less than about 5 percent by weight water than in one containing pure alcohol or an alcohol-water solvent system containing more than about 5 percent by weight water, e.g., 6.2 percent by weight water; and (2) that the presence of a glycol such as propylene glycol in an alcohol solvent system accelerates degradation of the compounds of formula 1; and (3) that an apparent pH of the alcohol-water solvent system of no more than about 5, preferably in the range of more than about 3 to less than about 5.0 enhances the stability of the compounds of formula I.

This invention provides a pharmaceutical composition for topical treatment of androgen-related disorders which comprises (a) an amount of a compound represented by formula I effective to topically treat the androgen-related disorders

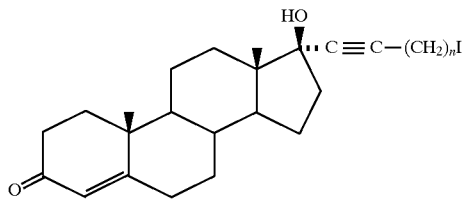

wherein n is an integer of 2 to 3; (b) an alcohol-water solvent system containing no more than about 5.0 weight percent water; and (c) a gelling agent in an amount sufficient to maintain the pharmaceutical composition in the form of a gel; and wherein the pharmaceutical composition has an apparent pH of less than or equal to about 5.

This invention further provides a pharmaceutical composition for topical treatment of androgen-related disorders which comprises:

(a) an amount of the compound represented by formula I effective to topically treat the androgen-related disorders

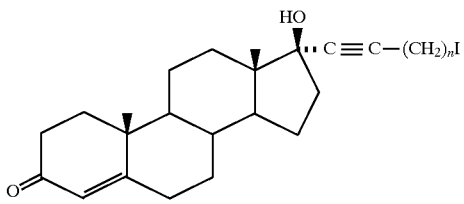

wherein n is an integer of 2 to 3;

(b) an ethanol-water solvent system containing no more than about 5.0 weight percent water;

(c) a buffer system capable of maintaining an apparent pH of the pharmaceutical composition at a value in the range of more than about 3 and less than about 5; and (4) an amount of a gelling agent sufficient to maintain the pharmaceutical composition in the form of a gel.

This invention further provides a pharmaceutical composition for topical treatment of androgen-related disorders which comprises (a) an amount of the compound represented by formula 11 effective to topically treat the androgen-related disorders

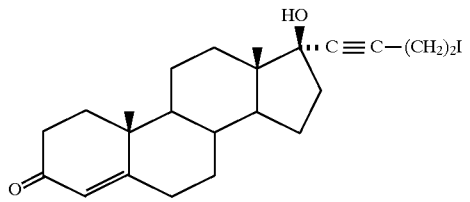

(b) an ethanol-water solvent system containing more than about 1.0 to about 4.0 percent by weight water; (c) a buffer system capable of maintaining an apparent pH of the pharmaceutical composition in the range of about 3.5 to about 4.5 and (d) an amount of a gelling agent sufficient to maintain the pharmaceutical composition in the form of a gel.

In a more preferred embodiment of this invention, there is provided an antiandrogenic gel composition comprising an amount of the compound represented by formula 11 effective to topically treat androgen-related conditions

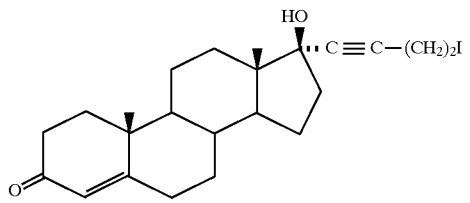

and having the name 17-α-(4-iodobutynyl)-17-β-hydroxy-4-androsten-3-one dissolved in an ethanol-water solvent system containing about 2.5 weight percent water and a buffer system capable of maintaining an apparent pH of the pharmaceutical composition at a value in the range of about 3.5 to 4.5 and an amount of a gelling agent sufficient to maintain the pharmaceutical composition in the form of a gel.

DETAILED DESCRIPTION

In the course of development of the stable gel compositions of this invention, we discovered that the antiandrogens represented by formulas I and II are soluble in alcohols such as ethanol, isopropanol, oleyl alcohol, propylene glycol, octanol and 2-methyl-1,4-pentandiol but are poorly soluble in water. Preformulation stability studies with the most preferred compound of formula II showed that the compound of formula II degrades rapidly at 50° C. in pure ethanol, ethanol:water (95:5, v/v) and ethanol: propylene glycol (90:10, v/v). The compound of formula II was stable to decomposition in an alcohol-water solvent system containing no more than about 5.0 weight percent water, preferably about 1.0 to about 4.0 weight percent of water, and more preferably about 2.0 to about 3.0 weight percent of water The alcohols found useful in the present invention include water soluble alcohols including $C_2$ to $C_8$ straight and branched chain alcohols. Use of ethanol or 2-propanol is preferred; use of ethanol is more preferred.

By the term "androgen-related conditions in humans" as used herein is meant those androgen-related conditions including acne, seborrhea, hirsutism, and androgenic alopecia, The buffer systems found useful in the present invention are those buffer systems which are water soluble buffer systems, especially those soluble in the alcohol-water solvent system useful in the present invention and capable of maintaining an apparent pH of the alcohol-water solvent system of no more than about 5, preferably in the range of more than about 3 to less than about 5, more preferably a pH in the range of about 3.5 to about 4.5, and most preferably at a pH of about 4. Typically suitable buffer systems include phosphoric acid/sodium phosphate monobasic; citric acid-sodium citrate and acetic acid/sodium acetate. Use of phosphoric acid/sodium phosphate monobasic is preferred. Other buffer systems capable of maintaining an apparent pH of about 3.5 to 4.5 in an alcohol-water system containing less than 10 weight percent water may also be used.

By the term "apparent pH value" as used herein in reference to the pharmaceutical compositions of the present invention is meant that the pH value of the stable pharmaceutical composition of the present invention which comprises a water-alcohol solvent system is measured using pH electrodes The gelling agents found useful in the present invention are those which can maintain the pharmaceutical composition of the present invention in the form of a gel. Typically suitable gelling agents include alkyl- and hydroxyalkyl ethers of cellulose including hydroxyethylcellulose, hydroxypropylcellulose, methylcellulose derivatives as well as carboxypolymethylene (which is highly ionic and slightly acidic) such as those carboxyvinylpolymers sold under the tradenames carbomers and carbopol. Use of hydroxypropylcellulose is preferred. The amount of gelling agent found effective to maintain the pharmaceutical compositions of this invention in the form of a gel is at least about 2 weight percent of the composition, preferably in the range of about 2 to about 5 weight percent, and more preferably about 2 to about 3 weight percent, and most preferably about 2.5 weight percent of the composition.

The topical pharmaceutical composition of the present invention are in the form of a gel containing an amount of the compounds of formulas 1 or 11 for the effective topical treatment of acne and other androgen-related disorders dissolved or dispersed, preferably dissolved, in an alcohol water solvent system having an apparent pH of less than about 5. In addition to the active ingredient, the alcohol-water solvent, the gelling agent and buffer system, pharmaceutically acceptable adjuvants, stabilizers, preservatives and surfactants may be included.

The pharmaceutical compositions of this invention are useful for the topical treatment of androgen-related conditions, e.g.,acne in humans. Typically the gel compositions would be applied topically twice a day, e.g., in the morning and in the evening, to the area of the skin where the acne and other androgen-related conditions lesions appear in an amount sufficient to lightly cover the entire affected area. The affected area of skin should be thoroughly cleansed prior to application of the pharmaceutical composition of the present invention. The amount of the compounds represented by formulas 1 and 11 effective to topically treat the androgen-related conditions, e.g.,acne varies from a dose level of about 0.01 $g/cm^2$ to about 0.1 $g/cm^2$ which may be applied as a thin film twice a day. Typical single doses include 0.3 g/30 $cm^2$, 0.6 g/60 $cm^2$ 1.0 g/100 $cm^2$ and 2 g/200 $cm^2$. The regimen should be continued for 4 to 16 weeks or until the androgen-related conditions, e.g. the acne lesions have satisfactorily responded. Once the twice daily regimen has provided such definite beneficial results, less frequent topical application (e.g. once daily) of the pharmaceutical composition of the present invention may be used to maintain the improvement in the androgen-related conditions, e.g. the acne lesions.

PHARMACEUTICAL COMPOSITIONS

The following examples illustrate the formulation and method of manufacture and packaging of compositions of the present invention. It will be apparent to those skilled in the art that many modifications thereof may be practical without departing from the purpose and intent of this invention.

EXAMPLE 1

The topical gel pharmaceutical compositions of this invention contain the following ingredient present in the listed amounts.

| Ingredient | Amount (mg/g) |
| --- | --- |
| Compound of formula II[1] | 8.00–12.00 |
| hydroxypropylcellulose NF[2] | 20.00–30.00 |
| sodium phosphate monobasic, USP | 0.025–0.035 |
| phosphoric acid, NF | 1.60–2.40 |
| water, purified (USP) | 19.0–29.0 |
| ethanol, USP | 929–951 |

1. The compound of formula 11 was prepared in accordance with the procedures of Example 2 and Scheme 2 of WO 94/26767, published Nov. 24, 1994.
2. Available under the tradename Klucel™ from Aqualon Company, 2711 Centervill Rd., Wilmington, Del. 19850.

The following procedure was used to prepare the composition:

1) Charge the water into an appropriate stainless steel container equipped with a suitable mixer.
2) Add the sodium phosphate into the water (step #1) and mix until it is dissolved.
3) Charge the alcohol into a large stainless steel vessel equipped with a suitable mixer.
4) Transfer aqueous solution (step #2) into the alcohol vessel (step #3) and start mixing.

5) Add the phosphoric acid into the mixing vessel (step #4) and mix for approximately 5 minutes.
6) Measure the pH of the alcohol/buffer solution (target pH=4.0±0.2). If the target pH is not achieved discard the material (alcohol/buffer solution).
7) If target pH is achieved, add the drug of formula 11 into the mixing vessel (step #5) and mix until the drug is completely dissolved.
8) Increase the agitation speed, add the Klucel HF slowly into the mixing vessel (avoid making lumps), and mix appropriately until the batch starts to thicken and Klucel HF is completely dispersed.
9) Decrease the agitation speed appropriately and continue mixing for approximately 15 minutes. Stop agitation and leave overnight.
10) Fill into the specified epoxy-lined aluminum tubes.
11) Store at 2° to 25° C.

EXAMPLE 2

The procedure of Example 1 was used to prepare the topical gel composition listed below.

| Ingredient | unit mg/g | Quantity per batch |
|---|---|---|
| compound of formula II[1] | 10.00 | 1.25 kg |
| hydroxypropylcellulose NF[2] | 25.00 | 3.125 kg |
| sodium phosphate monobasic, USP | 0.03 | 0.00375 kg |
| Phosphoric acid, NF | 2.00 | 0.25 kg |
| Water, purified (USP) | 24.07 | 3.00875 kg |
| ethanol USP | 938.90 | 117.3625 kg |
| TOTAL | 1000 | 125 kg |

1. The compound of formula II was prepared in accordance with the procedures of Example 2 and Scheme 2 of WO 94/26767, published Nov. 24, 1994..
2. The hydroxylcellulose used was Klucel HF available from Aqualon Company, 2711 Centervill Rd., Wilmington, DE 19850.

The most preferred gel pharmaceutical composition of the present invention prepared in accordance with the procedure of Example 2 was stable to decomposition of the compound of formula 11 when it was stored at a temperature of 25° C. for 24 months. The stability results are summarized in Table 1 hereinbelow.

TABLE 1

Stability of the Composition of Example 2 at 25° C. and 60% Relative Humidity

| Time (months) | Assay[1] % Compound of formula II as labeled strength |
|---|---|
| 0 | 103 |
| 3 | 102 |
| 6 | 102 |
| 9 | 101 |
| 12 | 100 |
| 18 | 104 |
| 24 | 98 |

[1]HPLC analysis.
[2]5% overcharge of II was added to the batch.

The stability of the compound of formula 11 in ethanol:water systems [95:5(v/v)] containing phosphate buffers capable of maintaining a pH of 4.0 to 5.0 was measured at temperatures of 300, 500 and 65° C. over a twelve (12) week period. The stability of the compound of formula 11 (as measured by HPLC assay) did not significantly change in the pH range of 4 to 5 as shown in the Table 2 hereinbelow.

TABLE 2

Stability of the Compound of Formula II[1] in ethanol:water[2] Containing Phosphate Buffers at Various pH Values and Temperatures.

| | pH = 4 Temperature (°C.) | | | pH = 4.5 Temperature (°C.) | | | pH = 5.0 Temperature (°C.) | | |
|---|---|---|---|---|---|---|---|---|---|
| Time (weeks) | 30° | 50° | 65° | 30° | 50° | 65° | 30° | 50° | 65° |
| 2 | — | 99 | 74 | — | 97 | 74 | — | 98 | 72 |
| 4 | 98 | 93 | 65 | 99 | 92 | 61 | 99 | 92 | 61 |
| 8 | 98 | 80 | 41 | 99 | 80 | 43 | 97 | 80 | 39 |
| 12 | 101 | — | — | 101 | — | — | 102 | — | — |

[1]Analysis of the compound of formula 1 by HPLC with an external standard.
[2]The ethanol:water is 95:5, v/v, equivalent to 93.8:6.2, w/w.

The stability of the compound of formula II (1% by weight) dissolved in an ethanol:water solvent system (95:5; v/v) containing a phosphate buffer in the aqueous phase was also measured at temperatures of 30°, 50° and 65° C. over a twelve (12) week period. The results summarized in the Table 3 herein below show that the stability of the compound of formula II is greatest at a pH of 4 (maintained by a phosphate buffer system) in an ethanol-water (97.5:2.5 v/v) solvent system

TABLE 3

Stability of the Compound of Formula II[1] in Various Ethanol:Water Solvent Systems containing a Phosphate Buffer at pH = 4 and at Temperatures of 30°, 50° and 65° C.

| | Ethanol:Water [97.5:2.5(v/v)][2] Temperature (°C.) | | | Ethanol:Water [95:2.5(v/v)][3] Temperature (°C.) | | | Ethanol:Water [92.5:7.5(v/v)][4] Temperature (°C.) | | |
|---|---|---|---|---|---|---|---|---|---|
| Time (weeks) | 30° | 50° | 65° | 30° | 50° | 65° | 30° | 50° | 65° |
| 2 | — | 98 | 76 | — | 99 | 74 | — | 97 | 76 |
| 4 | 99 | 92 | 66 | 98 | 93 | 65 | 98 | 92 | 60 |
| 8 | 99 | 83 | 50 | 98 | 80 | 41 | 98 | 77 | 36 |
| 12 | 100 | — | — | 101 | — | — | 100 | — | — |

[1]HPLC analysis
[2]96.9:3.1, w/w
[3]93.8:6.2, w/w
[4]90.7:9.3, w/w

What is claimed is:
1. A pharmaceutical composition for topical treatment of androgen-related disorders which comprises (a) an amount of a compound represented by formula I effective to topically treat the androgen-related disorders

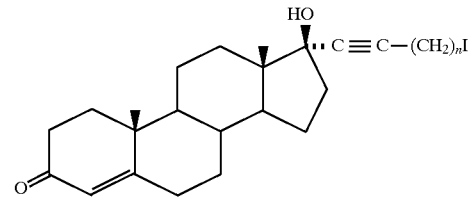

wherein n is an integer of 1 to 3; (b) an alcohol-water solvent system containing no more than about 5.0 weight percent water; and (c) a gelling agent in an amount sufficient to maintain the pharmaceutical composition in the form of a gel; and wherein the pharmaceutical composition has an apparent pH of less than or equal to about 5.

2. The pharmaceutical composition of claim 1 wherein the alcohol is ethanol.

3. The pharmaceutical composition of claim 1 wherein the pH is maintained in the range of more than about 3 and less than about 5.

4. The pharmaceutical composition of claim 1 wherein n in formula I is 2.

5. A pharmaceutical composition for topical treatment of androgen-related disorders which comprises:
(a) an amount of the compound represented by formula I effective to topically treat the androgen-related disorders.

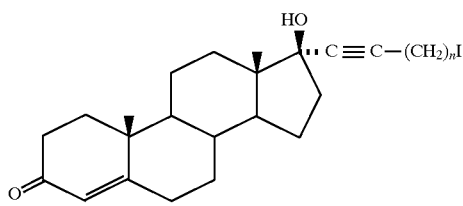

wherein n is an integer of 2 to 3;
(b) an ethanol-water solvent system containing no more than about 5.0 weight percent water;
(c) a buffer system capable of maintaining an apparent pH of the pharmaceutical composition at a value in the range of more than 3 to less than about 5; and
(4) an amount of a gelling agent sufficient to maintain the pharmaceutical composition in the form of a gel.

6. The pharmaceutical composition of claim 5 wherein n in formula 1 is 2.

7. The pharmaceutical composition of claim 5 wherein the ethanol-water solvent system contains about 1.0 to about 4.0 weight percent water.

8. The pharmaceutical composition of claim 5 wherein the apparent pH is in the range of about 3.5 to about 4.5.

9. A pharmaceutical composition for topical treatment of androgen-related disorders which comprises (a) an amount of the compound of formula II effective for the topical treatment of the androgen-related disorders;

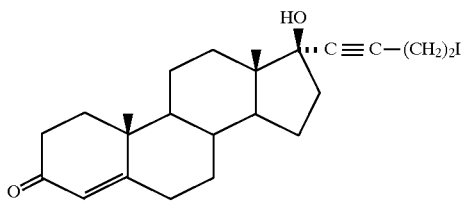

(b) an ethanol-water solvent system containing more than about 1.0 to about 4.0 percent by weight water; (c) a buffer system capable of maintaining an apparent pH of the pharmaceutical composition in the range of about 3.5 to 4.5 and (d) an amount of a gelling agent sufficient to maintain the pharmaceutical composition in the form of a gel.

10. The pharmaceutical composition of claim 9 wherein the gelling agent is a hydroxypropylcellulose.

11. The pharmaceutical composition of claim 9 comprising the ingredients present in the following amounts.

| Ingredient | Amount (mg/g) |
| --- | --- |
| Compound of formula II | 8.00–12.00 |
| hydroxypropylcellulose | 20.00–30.00 |
| sodium phosphate monobasic | 0.025–0.035 |
| phosphoric acid | 1.60–2.40 |
| water | 19.0–29.0 |
| ethanol | 929–951 |

12. The pharmaceutical composition of claim 9 comprising the ingredients present in the following amounts.

| Ingredient | Amount (mg/g) |
| --- | --- |
| Compound of formula II | 10.00 |
| hydroxypropylcellulose | 25.00 |
| sodium phosphate monobasic | 0.03 |
| phosphoric acid | 2.00 |
| water | 24.07 |
| Ethanol | 938.90 |

13. The pharmaceutical composition of claim 9 wherein the ethanol-water solvent system contains about 2.0 to about 3.0 weight percent water.

14. The pharmaceutical composition of claim 9 wherein the androgen-related condition is acne.

15. The pharmaceutical composition of claim 9 wherein the androgen-related condition is seborrhea.

16. The pharmaceutical composition of claim 9 wherein the androgen-related condition is hirsutism.

17. A method of treating acne which comprises administering to a human in need of such treating an amount of the pharmaceutical composition of claim 1 sufficient for effectively topically treating acne.

18. A method of treating seborrhea which comprises administering to a human in need of such treating an amount of the pharmaceutical composition of claim 1 sufficient for effectively topically treating seborrhea.

19. A method of treating hirsutism which comprises administering to a human in need of such treating an amount of the pharmaceutical composition of claim 1 sufficient for effectively topically treating hirsutism.

20. A method of treating androgenic alopecia which comprises administering to a human in need of such treating an amount of the pharmaceutical composition of claim 1 sufficient for effectively topically treating androgenic alopecia.

* * * * *